US00PP28567P2

(12) United States Plant Patent
Cho

(10) Patent No.: US PP28,567 P2
(45) Date of Patent: Oct. 24, 2017

(54) ***COLOCASIA* PLANT NAMED 'TROPICAL STORM'**

(50) Latin Name: *Colocasia esculenta*
Varietal Denomination: Tropical Storm

(71) Applicant: University of Hawaii, Honolulu, HI (US)

(72) Inventor: John J. Cho, Paia, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 14/999,838

(22) Filed: Jul. 7, 2016

(51) Int. Cl.
*A01H 5/00* (2006.01)

(52) U.S. Cl.
USPC ..... Plt./373

(58) Field of Classification Search
USPC ..... Plt./373
CPC ..... A01H 5/00
See application file for complete search history.

(56) References Cited

PUBLICATIONS http://www.greenhousegrower.com/varieties/16-new-foliage-plants-to-round-out-the-garden/; Jan. 17, 2016; 7 pages.*

* cited by examiner

*Primary Examiner* — Kent L Bell
(74) *Attorney, Agent, or Firm* — Bethany R. Roahrig; Barbara Campbell; Cochran Freund & Young, LLC

(57) ABSTRACT

A new cultivar of *Colocasia* plant named 'Tropical Storm' that is characterized by very compact, prolific basal branching and leaves which are purple-black in color except for a prominent contrasting cream-yellow central streak.

2 Drawing Sheets

STATEMENT REGARDING FEDERALLY SPONSORED RESEARCH

This invention was made with Government support under Grant No. 2005-31100-06015/HAW00948H awarded by the U.S. Department of Agriculture. The Government may have certain rights in this invention.

Genus and species: *Colocasia esculenta.*

Variety denomination: 'Tropical Storm'.

BACKGROUND OF THE NEW PLANT

The present invention relates to a new and distinct variety of *Colocasia* commonly known as the taro plant or elephant ears. *Colocasia* is grown as a food crop and for use as an ornamental plant in containers or in the landscape. The new cultivar is known botanically as *Colocasia esculenta* and will be referred to hereinafter by the cultivar name 'Tropical Storm'.

*Colocasia* is a tuberous rooted perennial which is native to tropical Asia and Polynesia. Native plants of *Colocasia* grow to 1.5 m to 2 m in height from starchy tubers. The leaves of *Colocasia* are heart-shaped and typically are very large in size.

The new *Colocasia* variety named 'Tropical Storm' is the product of a formal breeding program carried out in a cultivated area in Kula, Hi. The purpose of the breeding program is to develop new commercial varieties by combining attributes not found in currently commercially available varieties.

'Tropical Storm' is a seedling selection from the controlled pollination of the *Colocasia* variety named 'Black Magic' (unpatented) as the female parent variety by brushing pollen from the *Colocasia* variety 'Nancy's Revenge' (unpatented) as male parent. Seeds were allowed to mature within the developing fruits that formed after pollination. Seeds were removed around 45 days after pollination, and sown. From the resulting seedlings, the inventor selected 'Tropical Storm' in 2007.

'Tropical Storm' exhibits a compact plant habit with multiple basal branches giving rise to a high leaf count. The leaves of 'Tropical Storm' are purple-black in color except for a prominent contrasting cream-yellow central streak.

The most commonly employed means of asexual propagation of the genus *Colocasia* is the excision and replanting of a shoot which consists of the apical 1 cm to 2 cm portion of the plant corm with the attached basal 15 cm to 20 cm portion of the petiole. In regions of the world where *Colocasia* is grown, this plant shoot is known as a "huli", and the means of propagation is known as "huli propagation". Asexual propagation by "huli propagation" of 'Tropical Storm' began in 2007 at 454 Mauna Place, Kula, Hi. by the inventor using huli propagation whereby the apical shoots are separated from the plant by cutting the shoot at the top of the corm immediately above the newest leaf scar and planted. Evaluation in field and pot studies have shown the unique features of 'Tropical Storm' to be stable, uniform, and reproduces true to type in successive generations of asexual propagation.

SUMMARY

The following traits have been repeatedly observed and represent the distinguishing characteristics of the new *Colocasia* cultivar 'Tropical Storm'. These traits in combination set 'Tropical Storm' apart from all other existing varieties of *Colocasia* known to the inventor. 'Tropical Storm' has not been tested under all possible conditions and phenotypic differences may be observed with variations in environmental, climatic and cultural conditions, however, without any variance in genotype.

1. Plants of 'Tropical Storm' are very compact and exhibit prolific basal branching with high numbers of petioles and leaves.
2. The leaves of 'Tropical Storm' are purple-black in color, except for a prominent contrasting central streak which is cream-yellow in color.
3. The leaves of 'Tropical Storm' are presented slightly folded or cupped.
4. The leaves of 'Tropical Storm' are borne on glossy burgundy-red colored petioles.
5. The underside of the leaves of 'Tropical Storm' exhibit burgundy-red veins.
6. The upper and lower surfaces of the leaves of 'Tropical Storm' are matte.

BRIEF DESCRIPTION OF THE PHOTOGRAPHS

The accompanying color photographs illustrate the overall appearance of 'Tropical Storm' showing the colors as true as it is reasonably possible to obtain in colored reproductions of this type. Colors in the drawing may differ from the color values cited in the detailed botanical description, which accurately describe the actual colors of the new variety 'Tropical Storm'.

Figure 1:
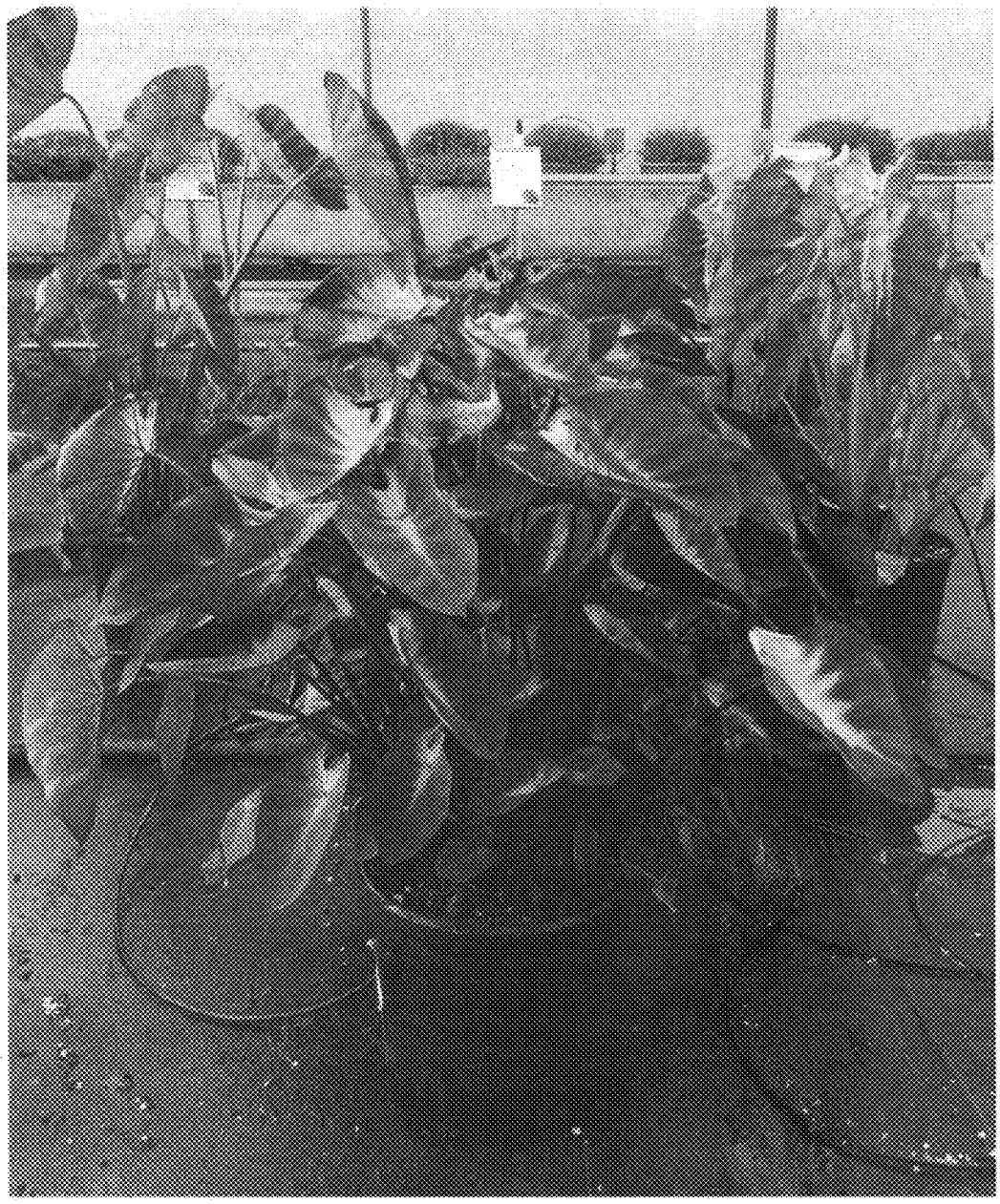
FIG. 1 shows a mature plant of 'Tropical Storm' in the foreground.
Figure 2:
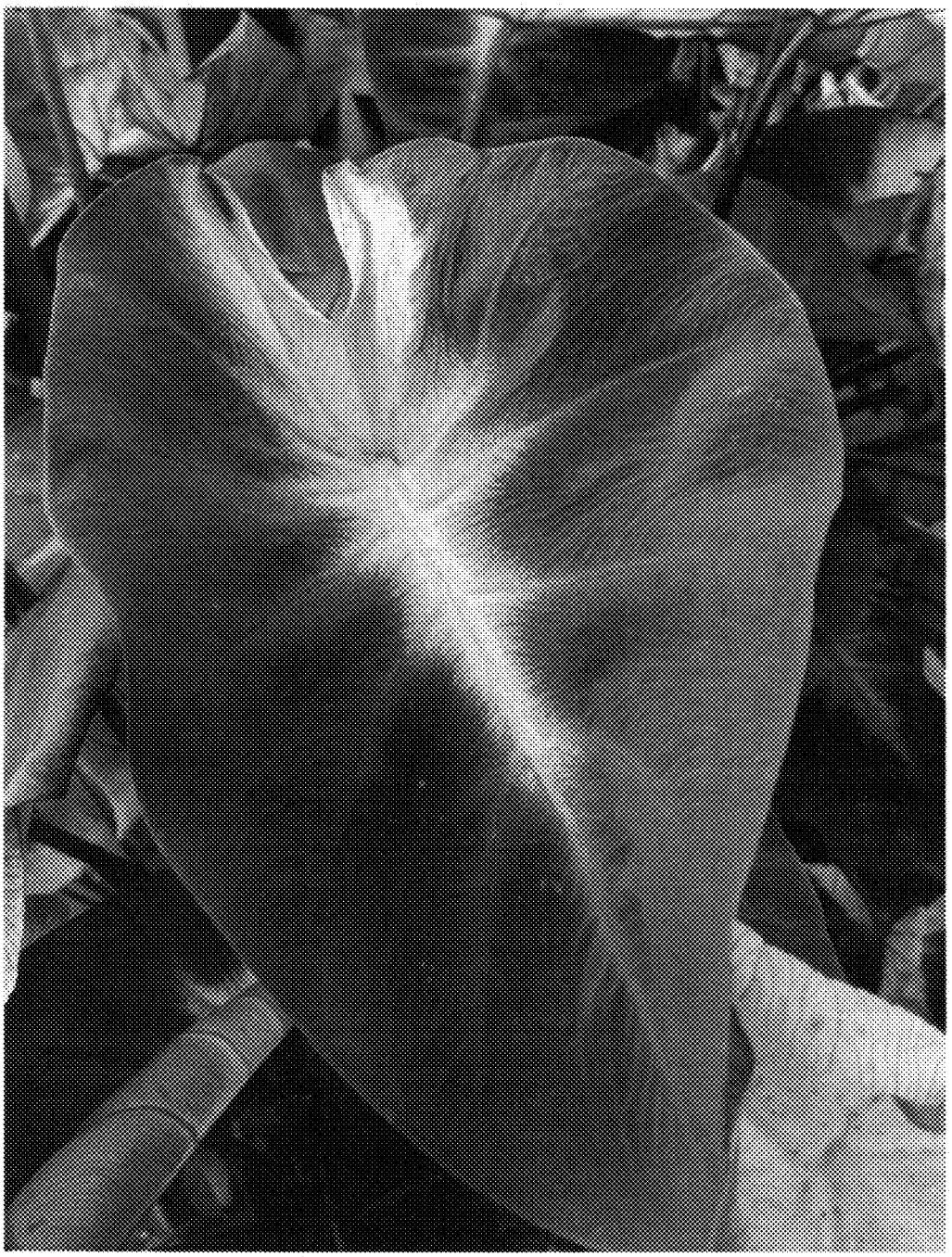
FIG. 2 shows a close-up of the leaf of 'Tropical Storm'.

The photographs were made from a plant which is approximately 12 months old from a tissue culture division and which had been grown outdoors in Santa Barbara, Calif. No growth regulators had been applied.

BOTANICAL DESCRIPTION OF THE PLANT

The following is a detailed description of the new *Colocasia* plant named 'Tropical Storm'. Data was collected from a plant which was 12 months old from a tissue culture division and grown outside in Santa Barbara, Calif. The color determinations are in accordance with The 2007 edition of The Royal Horticultural Society Color Chart, London, England, except where general color terms of ordinary dictionary significance are used. The growing requirements are similar to other *Colocasia*.

Botanical classification:

*Genus.*—*Colocasia.*

*Species.*—*esculenta.*

*Variety.*—'Tropical Storm'.

*Common name.*—Taro or elephant ears.

Parentage:

*Female parent.*—*Colocasia* 'Black Magic' (unpatented).

*Male parent.*—*Colocasia* 'Nancy's Revenge' (unpatented).

Plant description:

*Use.*—Container or landscape plant.

*Cultural requirements.*—In common with all *Colocasia*, 'Tropical Storm' thrives in high temperatures (above 70° F.), in full sun or partial shade, and is most vigorous when well-watered.

*Root system.*—Tuberous.

*Roots.*—Fleshy, up to 2 mm in diameter, with fibrous and fine lateral roots; color 155B.

*Root development.*—At soil temperatures 20° C. to 25° C., root initials are evident within 3 days. Roots will reach the edge of a 1 gallon container in 14 days.

*Plant vigor.*—Vigorous basal branching, forming dense canopy of leaves and stems.

*Plant growth habit.*—Upright, domed, non-spreading.

*Plant growth rate.*—A one gallon container plant may be produced in 12 to 16 weeks from a 4 cm cell transplant.

*Plant description.*—Once a huli or corm is introduced into the soil and the plant is established, additional corms or cormels are produced, attached to the original corm. These cormels give rise to new lateral shoots. A one year old plant of 'Tropical Storm' produces 25 to 35 lateral shoots. Lateral shoots begin to appear above soil level about 6 to 8 weeks after planting of the initial plant.

*Corm* (*formed at base of each petiole or huli*).—Shape and dimensions: Short cylindrical, 2 cm to 3 cm in diameter, 1 cm in height. Surface texture: Rough with root initials (eyes). Color ranges between N186A and 202A.

*Cormels* (*arising from established corm, forming base of new lateral shoot*).—Shape and dimensions: Short cylindrical, 1.0 cm to 2.5 cm in diameter, 0.5 cm in height. Surface texture: Rough with root initials (eyes). Color ranges between N186A and 202A.

*Plant dimensions.*—45 cm to 60 cm in height and 45 cm to 60 cm in width.

*Plant hardiness.*—USDA Zone 7b.

*Propagation.*—Propagation is accomplished by huli propagation and by tissue culture.

*Time to develop daughter plants.*—Appear above soil around 2 to 3 months after planting.

*Crop time.*—1.5 to 2.5 months.

Foliage (lateral shoots):

*Petioles.*—Shape: Round section. Petiole base enclosed within short clasping sheath which is open along its uppermost aspect. Length: 12 cm to 30 cm. Diameter: 2.5 mm (just below attachment to lamina), 4 mm (as petiole emerges from sheath), 6 mm (inside the sheath). Strength: Strong, stiff. Color: 187B. Surface texture: Glabrous, glossy. Sap color: Colorless.

*Leaf.*—Number: Each lateral shoot bears 1 to 5 leaves at a time. Observed plant has 50 to 60 leaves of all ages. Dimensions at maturity: 17 cm to 20 cm in length and 12 cm to 15 cm in width. Average leaf sinus depth (Mature leaf): 5.5 cm. Attitude: Oblique. Aspect: Erect with apex down. Leaf slightly folded or cupped. Shape: Sagittate. Margins: Entire, slightly undulating. Apex: Acuminate, extends 4 mm. Base: Peltate. Attachment: Petiolate with characteristic tissue formed at junction of leaf blade with the upper termination of the petiole. This area of the leaf tissue is also known as the "piko" and is evident by virtue of its upper surface color being similar to the color of the petiole. The principal veins radiate from the piko. Piko color: 187B. Leaf texture: Matte (both surfaces). Leaf color (except central cream-yellow streak): Adaxial surface: Ranges between N187A and N186A. Abaxial surface: N187B. Leaf color (cream-yellow streak): Adaxial surface: Ranges between 4A and 4C. Abaxial surface (individual leaves): 154C and 1A. Presence of cream-yellow streak: Not present on either surface of first 3 (approximately), leaves of each lateral shoot. From $3^{rd}$ or $4^{th}$ leaf, cream-yellow streak increasingly evident on adaxial surface, diffused on abaxial surface. Arrangement and dimensions of cream-yellow streak: Adaxial surface: Dagger-shaped, extending from leaf base (pair) along central vein and partially along lateral veins. Streak does not extend to apex. Length: 10 cm to 12 cm. Width (leaf base): 5 cm to 7 cm. Abaxial surface: Barely apparent. Appears as green-yellow coloration along abaxial central vein and lateral veins. Venation: Palmate. Veins: Three principal veins radiating from the piko: one midrib extending 13 cm to 16 cm from the piko to the tip of the lamina, and one pair of veins extending towards each of the basal lobe margins. Up to eight pairs of secondary veins radiating from the region of the piko and from the midrib. Vein color (both surfaces): 187B.

Inflorescence flowers, reproductive organs and seed: None observed.

Diseases and pests: In common with *Colocasias* in general, 'Tropical Storm' is susceptible to attack by *Tetranychus urticae*, commonly known as red spider mite. Otherwise, the inventor has not observed that 'Tropical Storm' is more or less susceptible to pests or diseases than other cultivars of the genus.

COMPARISON WITH PARENTAL LINES

Whereas both 'Black Magic' and 'Nancy's Revenge' reach a mature height of 1.5 m to 2.0 m, 'Tropical Storm' is compact and reaches a mature height of 0.45 m to 0.60 m. The leaves of 'Tropical Storm' are proportionately smaller than the leaves of either parent. In addition, the leaves of 'Black Magic' are entirely dark purple-black in color and do not exhibit the prominent central cream-yellow streak which characterizes 'Tropical Storm'. The leaves of 'Nancy's Revenge' do exhibit a central cream-yellow streak: however, the predominant foliage color of 'Nancy's Revenge' is green, whereas the leaves of 'Tropical Storm' are predominantly purple-black in color.

COMPARISON WITH KNOWN VARIETY

The closest comparison variety in commerce known to the inventor is the male parent variety *Colocasia* 'Nancy's Revenge' whose leaves bear a similarly prominent cream-yellow central streak. However, the predominant leaf color of 'Nancy's revenge' is green and the plant height of 'Nancy's Revenge' is 1.5 m to 2.0 m.

I claim:

1. A new and distinct cultivar of *Colocasia* plant named 'Tropical Storm' as described and illustrated herein.

* * * * *